United States Patent
Blischak

(10) Patent No.: US 7,962,224 B1
(45) Date of Patent: Jun. 14, 2011

(54) STIMULATION LEAD, STIMULATION SYSTEM, AND METHOD FOR LIMITING MRI-INDUCED CURRENT IN A STIMULATION LEAD

(75) Inventor: Brian Blischak, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 629 days.

(21) Appl. No.: 12/026,078

(22) Filed: Feb. 5, 2008

Related U.S. Application Data

(60) Provisional application No. 60/888,184, filed on Feb. 5, 2007.

(51) Int. Cl.
*A61N 1/05* (2006.01)

(52) U.S. Cl. .................. 607/116; 607/1; 607/2; 607/63; 607/115

(58) Field of Classification Search .......................... None
See application file for complete search history.

(56) References Cited

U.S. PATENT DOCUMENTS

| | | | |
|---|---|---|---|
| 5,217,010 A | 6/1993 | Tsitlik et al. | |
| 6,985,775 B2 | 1/2006 | Reinke et al. | |
| 7,174,219 B2 | 2/2007 | Wahlstrand et al. | |
| 7,363,090 B2 | 4/2008 | Halperin et al. | |
| 2003/0083726 A1 | 5/2003 | Zeijlemaker et al. | |
| 2003/0144716 A1 | 7/2003 | Reinke et al. | |
| 2003/0144720 A1 | 7/2003 | Villaseca et al. | |
| 2005/0020873 A1 * | 1/2005 | Berrang et al. ................. 600/25 |
| 2005/0027340 A1 | 2/2005 | Schrom et al. | |
| 2005/0222656 A1 | 10/2005 | Wahlstrand et al. | |
| 2005/0222657 A1 | 10/2005 | Wahlstrand et al. | |
| 2005/0222658 A1 * | 10/2005 | Hoegh et al. .................. 607/116 |
| 2005/0222659 A1 | 10/2005 | Olsen et al. | |
| 2006/0229693 A1 | 10/2006 | Bauer et al. | |
| 2006/0247747 A1 | 11/2006 | Olsen et al. | |
| 2006/0247748 A1 | 11/2006 | Wahlstrand et al. | |

(Continued)

FOREIGN PATENT DOCUMENTS

EP       0 617 981 A1 * 10/1994

OTHER PUBLICATIONS

Buchli R., et al., "Heating Effects of Metallic Implants by MRI Examinations," Magnetic Resonance in Medicine, 7, 255-261 (1988).

(Continued)

*Primary Examiner* — Carl H Layno
*Assistant Examiner* — Deborah Malamud
(74) *Attorney, Agent, or Firm* — Christopher S. L. Crawford; Craig Hoersten; Melissa Acosta

(57) ABSTRACT

In one embodiment, a stimulation lead for delivering electrical pulses from a pulse generator to tissue of a patient, comprises: a plurality of electrodes; a plurality of terminals; a plurality of conductors electrically coupling the plurality of electrodes with the plurality of terminals; a lead body of insulative material for enclosing the plurality of conductors; and at least one magnetic-field actuated switch for limiting MRI-induced current between the plurality of electrodes and the plurality of terminals, wherein the magnetic-field actuated switch is actuated by magnetostrictive material.

13 Claims, 4 Drawing Sheets

U.S. PATENT DOCUMENTS

| | | |
|---|---|---|
| 2007/0088416 A1 | 4/2007 | Atalar et al. |
| 2007/0112398 A1 | 5/2007 | Stevenson et al. |
| 2007/0185556 A1 | 8/2007 | Williams et al. |
| 2007/0208383 A1 | 9/2007 | Williams |
| 2007/0299490 A1 | 12/2007 | Yang et al. |
| 2008/0009905 A1 | 1/2008 | Zeijlemaker |
| 2008/0033497 A1 | 2/2008 | Bulkes et al. |
| 2008/0116997 A1 | 5/2008 | Dabney et al. |
| 2008/0119919 A1 | 5/2008 | Atalar et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |

OTHER PUBLICATIONS

Bhachu, Dewinder S., et al., "Implantable Pulse Generators (Pacemakers) and Electrodes: Safety in the Magnetic Resonance Imaging Scanner Environment," Journal of Magnetic Resonance Imaging, 12:201-204 (2000).

Finelli, Daniel, et al., "MR Imaging-Related Heating of Deep Brain Stimulation Electrodes: In Vitro Study," Am. J. Neuroradiol, 23:1795-1802, Nov./Dec. 2002.

Ho, Henry S., "Safety of Metallic Implants in Magnetic Resonance Imaging," Journal of Magnetic Resonance Imaging, 14: 472-477 (2001).

* cited by examiner

STIMULATION LEAD, STIMULATION SYSTEM, AND METHOD FOR LIMITING MRI-INDUCED CURRENT IN A STIMULATION LEAD

RELATED APPLICATION

This application claims the benefit of U.S. Provisional Application No. 60/888,184, filed Feb. 5, 2007, the disclosure of which is incorporated herein by reference.

TECHNICAL FIELD

The present application is generally related to limiting the amount of MRI-induced current that flows between the surrounding tissue and a stimulation lead such as a neurostimulation lead, a cardiac stimulation lead, and/or the like.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include cardiac rhythm management, deep brain stimulation, cortical stimulation, cochlear nerve stimulation, peripheral nerve stimulation, vagal nerve stimulation, sacral nerve stimulation, optical nerve stimulation, functional electrical stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or several leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

There are concerns related to the compatibility of neurostimulation systems with magnetic resonance imaging (MRI). MRI generates cross-sectional images of the human body by using nuclear magnetic resonance (NMR). The MRI process begins with positioning the patient in a strong, uniform magnetic field. The uniform magnetic field polarizes the nuclear magnetic moments of atomic nuclei by forcing their spins into one of two possible orientations. Then an appropriately polarized pulsed RF field, applied at a resonant frequency, forces spin transitions between the two orientations. Energy is imparted into the nuclei during the spin transitions. The imparted energy is radiated from the nuclei as the nuclei "relax" to their previous magnetic state. The radiated energy is received by a receiving coil and processed to determine the characteristics of the tissue from which the radiated energy originated to generate the intra-body images.

Currently, most neurostimulation systems are designated as being contraindicated for MRI, because the time-varying magnetic RF field causes the induction of current which, in turn, can cause significant heating of patient tissue due to the presence of metal in various system components. The induced current can be "eddy current" and/or current caused by the "antenna effect." As used herein, the phrase "MRI-induced current" refers to eddy current and/or current caused by the antenna effect.

"Eddy current" refers to current caused by the change in magnetic flux due to the time-varying RF magnetic field across an area bounding conductive material (i.e., patient tissue). The time-varying magnetic RF field induces current within the tissue of a patient that flows in closed-paths. When a conventional pulse generator and a conventional implantable lead are placed within tissue in which eddy currents are present, the implantable lead and the pulse generator provide a low impedance path for the flow of current. Electrodes of the lead provide conductive surfaces that are adjacent to current paths within the tissue of the patient. The electrodes are coupled to the pulse generator through a wire conductor within the implantable lead. The metallic housing (the "can") of the pulse generator provides a conductive surface in the tissue in which eddy currents are present. Thus, current can flow from the tissue through the electrodes and out the metallic housing of the pulse generator—or vice versa. Because of the low impedance path and the relatively small surface area of each electrode, the current density in the patient tissue adjacent to the electrodes can be relatively high. Accordingly, resistive heating of the tissue adjacent to the electrodes can be high and can cause significant, irreversible tissue damage.

Also, the "antenna effect" can cause current to be induced which can result in undesired heating of tissue. Specifically, depending upon the length of the stimulation lead and its orientation relative to the time-varying magnetic RF field, the wire conductors of the stimulation lead can each function as an antenna and a resonant standing wave can be developed in each wire. A relatively large potential difference can result from the standing wave thereby causing relatively high current density and, hence, heating of tissue adjacent to the electrodes of the stimulation lead.

SUMMARY

In one embodiment, a stimulation lead for delivering electrical pulses from a pulse generator to tissue of a patient, comprises: a plurality of electrodes; a plurality of terminals; a plurality of conductors electrically coupling the plurality of electrodes with the plurality of terminals; a lead body of insulative material for enclosing the plurality of conductors; and at least one magnetic-field actuated switch for limiting the amount of MRI-induced current that flows between the surrounding tissue and the lead, wherein the magnetic-field actuated switch is actuated by magnetostrictive material.

In one embodiment, an implantable pulse generator for generating electrical pulses to stimulate tissue of a patient, comprises: pulse generating circuitry for generating electrical pulses; output circuitry for coupling electrical pulses from the pulse generating circuitry to output contacts adapted for electrical coupling to terminal contacts of one or more stimulation leads; and at least one magnetic-field actuated switch for modifying a circuit path between the pulse generating circuitry and the output contacts to limit MRI-induced current between the pulse generating circuitry and the output contacts, wherein the magnetic-field actuated switch is actuated by magnetostrictive material.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit or scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
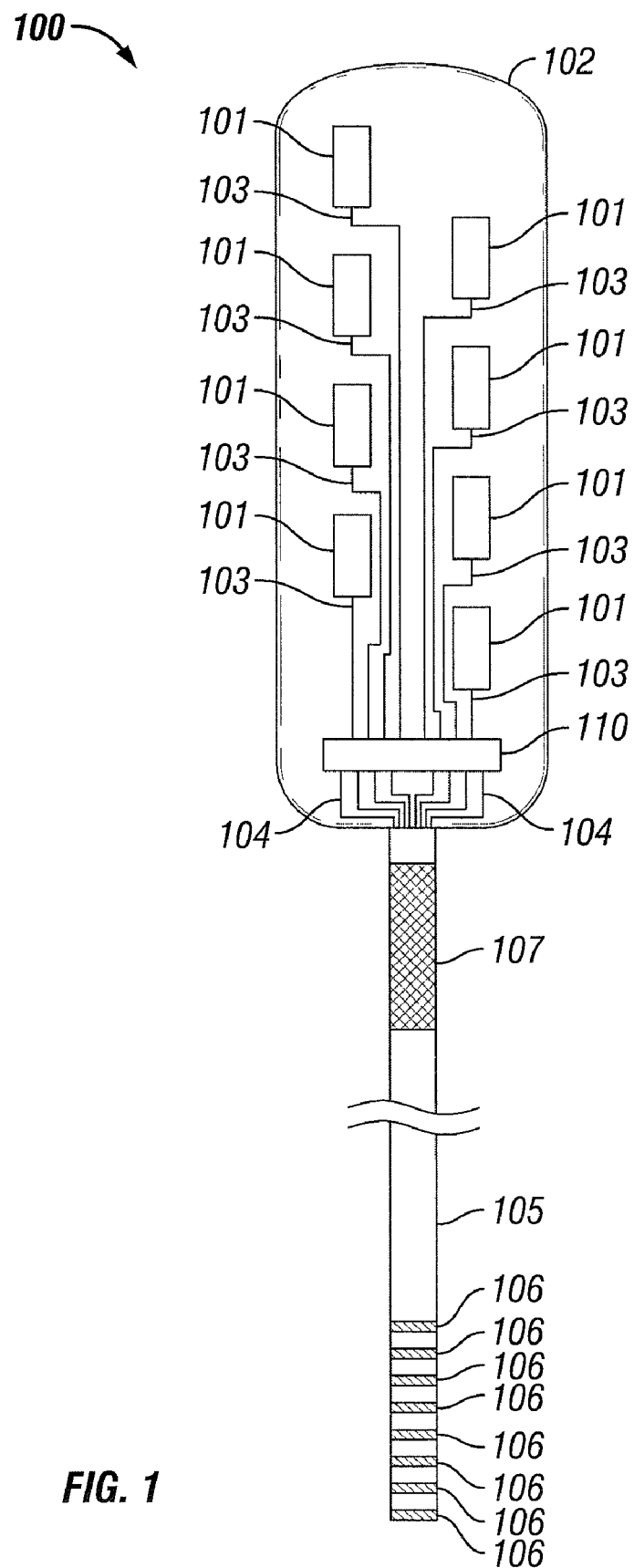
FIG. 1 depicts a paddle lead according to one representative embodiment.

FIG. 1 depicts paddle lead 100 for limiting MRI-induced current according to one representative embodiment. Paddle lead 100 is preferably adapted for spinal cord stimulation. However, paddle lead 100 may be utilized for any suitable stimulation application such as cortical stimulation, peripheral nerve stimulation, functional electrical stimulation as examples. Also, although some embodiments are discussed in the context of various types of neurostimulation, alternative embodiments can be employed in any implantable medical device or system that applies electrical pulses to patient tissue and/or measures physiological signals such as cardiac pacing systems, defibrillators, gastric pacing systems, etc.

Paddle lead 100 comprises a plurality of electrodes 101 implemented on paddle structure 102 at the distal end of lead 100. In the specific embodiment shown in FIG. 1, two columns of electrodes 101 are employed with four electrodes in each column. The two columns of electrodes 101 are staggered with respect to each other. Any suitable number of electrodes and any suitable electrode pattern can be employed for paddle 100 according to other representative embodiments. Also, paddle lead 102 may optionally comprise indifferent electrode 107 to allow MRI-induced current to be more safely distributed over a greater surface area.

Paddle structure 102 may be fabricated using any suitable material as known to those skilled in the art. Such materials may include polyetheretherketone (PEEK) and polyetherketone ketone (PEKK), and silicone rubber adapted to be disposed within the human body. Further structural elements can be included within paddle structure 102 such as a fiberglass or metal mesh (not shown) to provide structural rigidity to paddle structure 102 and/or to provide a desired shape to paddle structure 102. For example, the side of paddle structure 102 opposite to the side where electrodes 101 are disposed may possess a curve corresponding to the posterior shape of the epidural space 17. The side of paddle structure 102 where the electrodes are disposed may be shaped to allow electrodes 101 to be positioned substantially tangential to the dura. "Wing" structures (not shown) extending above the surface may be provided to assist in retaining paddle structure 102 within an optimal position within the epidural space.

The proximal end of paddle lead 100 couples to an implantable pulse generator, intermediate wiring, or other stimulation device (not shown) as known to those skilled in the art. The stimulation pulses produced by the implantable pulse generator are received by terminals 106 and are conducted through lead body 105 via wire conductors (not shown). The wire conductors may take the form of solid conductors, drawn-filled-tube (DFT), drawn-brazed-strand (DBS), stranded conductors or cables, ribbon conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. An insulative coating can be optionally applied over the metal material of conductors.

Lead body 105 is typically fabricated by winding the wire conductors around a mandrel (with or without one or more insulative layers). One or more outer layers of insulative material are applied over the wound conductive wires. The insulative material may include silicone, polyurethane, polyethylene, polyimide, polyvinylchloride, PTFT, EFTE, or other suitable materials known to those skilled in the art. The insulative material and conductive wires may be subjected to heat and pressure (e.g., using shrink wrap tubing) to cause the insulative material to flow and fuse. Such techniques for fabricating lead body 105 are discussed in greater detail in U.S. patent application Ser. No. 10/630,233, entitled "SYSTEM AND METHOD FOR PROVIDING A MEDICAL LEAD BODY HAVING DUAL CONDUCTOR LAYERS," which is incorporated herein by reference, although any other suitable technique for fabrication of lead body 105 may be employed. The wire conductors of lead body 105 terminate at the distal end of lead body and are electrically coupled to an initial set of wires 104 within paddle structure 102.

The initial set of wire conductors 104 are electrically coupled through switch structure 110 to a second set of wire conductors 103 which are, in turn, coupled to the respective electrodes 101. Switch structure 110 is operable to selectively control one or several electrical connections to limit MRI-induced current from flowing through electrodes 103 to the wire conductors of lead body 105. Switch structure 110 is actuated or controlled in response to the detection of a magnetic field. In one embodiment, the magnetic material of switch structure 110 is adapted to automatically to rotate to align with the magnetic field. Such rotation can be accomplished by attaching the magnetic material to a gimble with a magnet on it so that an external magnet will spin the gimble.

Switch structure 110 is preferably actuated or controlled using magnetostrictive material. A preferred magneto strictive material is the Terfenol-D material (a terbium, iron, and dysprosium alloy) which is commercially available. The magnetostrictive effect is molecular in origin and is caused by the rotation of small magnetic domains that result in internal strains within the material. These strains cause a positive expansion of the material in parallel to the magnetic field. As the field strength increases, more domains within the material rotate and become aligned until magnetic saturation is reached. If the field is reversed, the direction of the domains is also reversed, but the strain within the material still results in a positive expansion in the field direction. The mechanical response is relatively fast (e.g., microseconds) and magnetostrictive material conserves volume (e.g., the diameter decreases as the length grows).

Switch structure 110 may be utilized to control, mitigate, or otherwise limit MRI-induced current in a number of ways. Switch 110 may be implemented using any suitable mechanical, electrical, or electro-mechanical design as examples. For example, switch structure 110 could simply be implemented to allow each wire 104 to electrically contact a corresponding wire 103 in the absence of a magnetic field and to separate each wire 104 from its corresponding wire 103 in the presence of a sufficiently strong magnetic field due to the expansion of the magnetostrictive material. Effectively, an open circuit would be created for each electrode 103 in the presence of a sufficiently strong magnetic field thereby preventing the conduction of MRI-induced current.

In another embodiment, switch structure 110 is operable to change an impedance in the current path between each wire 104 and a corresponding wire 103 in response to the detection of a sufficiently strong magnetic field. A change in resistance, inductance, or capacitance could be affected under the controller of switch structure 110. Alternatively, switch structure 110 could be implemented to control MRI-induced current by shunting the MRI-induced current to an indifferent electrode. Preferably, the indifferent electrode possesses a surface area greater than the surface area of electrodes 103. By utilizing a greater surface area, the current density is reduced and the amount of resistive heating is also reduced. Switch structure 110 could be employed to allow the wire conductors within lead body 105 to be coupled to suitable circuitry to "de-tune" the wire conductors to the MRI frequency so that the antenna effect captures less energy. Specifically, switch structure 110 could be employed somewhere within the middle of the lead to separate the wire conductors thereby effectively shortening electrical length of the wire conductors.

FIGS. 2A-2E depict circuit connection 200 that may be included within switch structure 110 according to one representative embodiment. Specifically, a respective circuit connection 200 can be included within switch structure 110 between each wire 103 and a corresponding wire 104 to control the conduction of MRI-induced current. In some embodiments, circuit connection 200 is preferably fabricated as part of a micro-electrical-mechanical (MEMs) device.

Figure 2A:
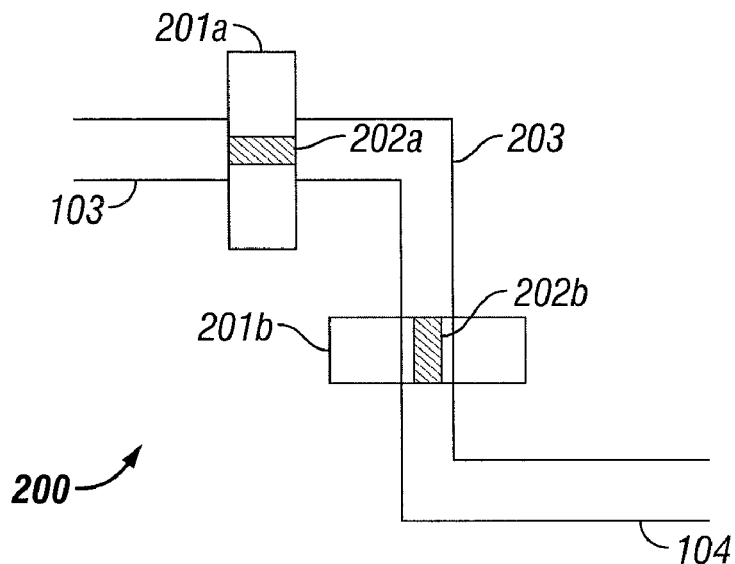
FIGS. 2A-2E depict a circuit connection that is controllably interrupted in response to the detection of a sufficiently strong magnetic field according to one representative embodiment.

FIG. 2A depicts circuit connection 200 that is controllably interrupted in response to the detection of a sufficiently strong magnetic field according to one representative embodiment. Circuit connection 200 is controlled by magnetostrictive elements 201a and 201b. FIG. 2A depicts circuit connection 200 in the absence of a magnetic field. As shown in FIG. 2A, wire 103 is in electrical and mechanical contact with conductor 202a which is mechanically coupled to magnetostrictive element 201a. Also, wire 104 is in electrical and mechanical contact with conductor 202b which is mechanically coupled to magnetostrictive element 201b. Intermediate conductor 203 is in electrical and mechanical contact with conductors 202a and 202b. Accordingly, current is able to flow from wire 103 through conductor 202a, intermediate conductor 203, conductor 202b, and wire 104. Magnetostrictive elements 201a and 201b are disposed in an orthogonal relationship to each other.

Figure 2B:
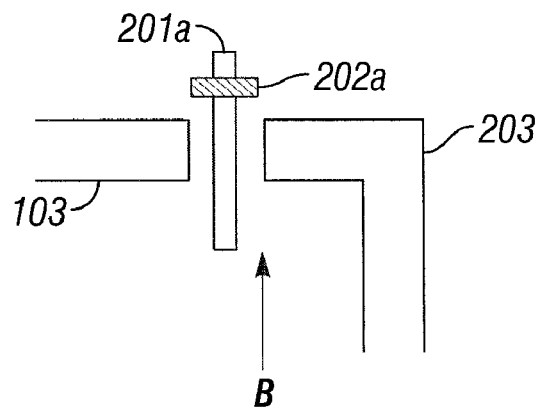

FIG. 2B depicts the "upper" portion of circuit connection 200 in the presence of a sufficiently strong magnetic field in the direction parallel to magnetostrictive element 201a. The magnetic field (e.g., the static magnetic field of a commercially available MRI system) causes magnetostrictive element 201a to expand in the direction of the magnetic field. Conductor 202a is translated by the expansion and is no longer in mechanical and electrical contact with wire 103 and intermediate conductor 203. Accordingly, current can no longer flow through circuit connection 200 in the presence of the magnetic field. If the magnetic field is in the direction opposite the direction shown in FIG. 2A, magnetostrictive element 201a would expand while conductor 202a would be translated in the opposite direction. Nonetheless, conductor 202a would no longer be in electrical and mechanical contact with wire 103 and intermediate conductor 203.

Figure 2C:
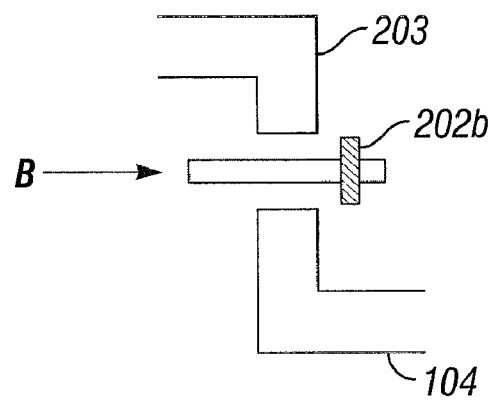

FIG. 2C depicts the "lower" portion of circuit connection 200 in the presence of a sufficiently strong magnetic field in the direction parallel to magnetostrictive element 201b. The magnetic field causes magnetostrictive element 201b to expand in the direction of the magnetic field. Conductor 202b is translated by the expansion and is no longer in mechanical and electrical contact with wire 104 and intermediate conductor 203. Accordingly, current can no longer flow through circuit connection 200 in the presence of the magnetic field.

Figure 2D:
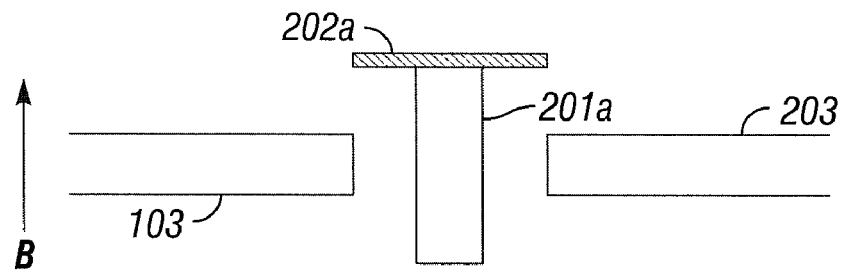

FIG. 2D depicts the "upper" portion of circuit connection 200 in the presence of a sufficiently strong magnetic field in the direction orthogonal to both magnetostrictive elements 201a and 201b. As shown in FIG. 2D, magnetostrictive element 201a expands "up" in the direction of the magnetic field. Conductor 202a is translated by the expansion and is no longer in mechanical and electrical contact with wire 103 and intermediate conductor 203. Accordingly, current can no longer flow through circuit connection 200 in the presence of the magnetic field.

Figure 2E:
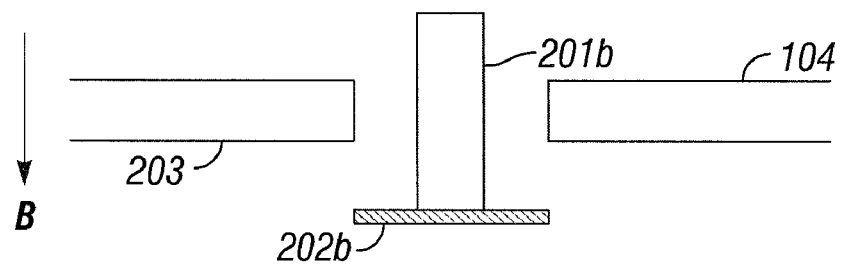

FIG. 2E depicts the "lower" portion of circuit connection 200 in the presence of a sufficiently strong magnetic field in the direction opposite to the field shown in FIG. 2D. As shown in FIG. 2E, magnetostrictive element 201b expands "down" in the direction of the magnetic field. Conductor 202b is translated by the expansion and is no longer in mechanical and electrical contact with wire 104 and intermediate conductor 203. Accordingly, current can no longer flow through circuit connection 200 in the presence of the magnetic field.

By utilizing the arrangement of circuit connection 200, switch structure 110 is able to prevent the conduction of MRI-induced current due to the presence of the strong static magnetic field of the MRI system without regard to the specific direction of the magnetic field relative to the orientation of paddle structure 102.

Figure 3:
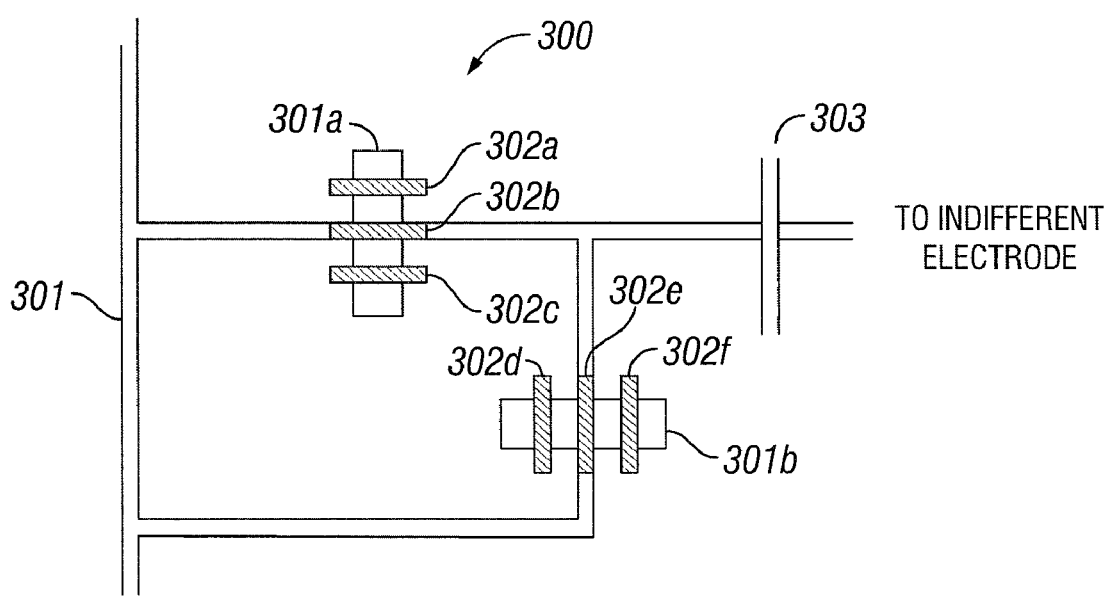
FIG. 3 depicts a connection circuit that is controllably established in response to the detection of a sufficiently strong magnetic field according to one representative embodiment.

FIG. 3 depicts connection circuit 300 according to another representative embodiment. A plurality of connection circuits 300 could be implemented within switching structure 110 for each circuit path electrically coupled to the plurality of electrodes 101. Connection circuit 300 is adapted such that an electrical connection is not maintained in the absence of a magnetic field. Instead, when a sufficiently strong magnetic field is present, connection circuit 300 establishes an electrical connection to shunt current from line 301 (which could be a respective wire 103 or wire 104) to an indifferent electrode.

That is, connection circuit 300 functions as a switching element to selectively switch MRI-induced current to the indifferent electrode.

As shown in FIG. 3, magnetostrictive element 301a is mechanically coupled to three conductors 302a, 302b, and 302c. Conductors 302a and 303b are adapted such that a magnetic field parallel to magnetostrictive element 301 causes one of these conductors to establish an electrical connection. Magnetostrictive element 301b is co-planar and orthogonal to magnetostrictive element 301a. Magnetostrictive element 301b is mechanically coupled to three conductors 302d, 302e, and 302f. Conductors 302d and 303f are adapted such that a magnetic field parallel to magnetostrictive element 301 causes one of these conductors to establish an electrical connection. Although not visible in the view shown in FIG. 3, conductors 302b and 302e are preferably offset in the vertical direction such that conductors 302b and 302e do not make an electrical connection in the absence of a magnetic field, i.e., one is offset "above" and the other is offset "below." When a sufficiently strong magnetic field in the out-of-plane direction is present, one of conductors 302b and 302e make an electrical connection thereby allowing current flow to the indifferent electrode.

Circuits 200 and 300 are provided by way of example. Any suitable circuit design in which a circuit connection is controllably made or disconnected in response to detection of a magnetic field may be utilized according to representative embodiments. Levers or other mechanical components can be utilized to scale the dimensional changes of the magnetostrictive material if deemed appropriate for a particular lead or system design. Furthermore, the actuation or control by the magnetostrictive material may be utilized to control multiple poles of a respective switch.

Although switching structure 110 has been discussed as being implemented at the proximal end of paddle structure 102, switching structure 110 (or parts thereof) could be implemented at any suitable location within lead 100. For example, respective connection circuits could be employed anywhere along the length of lead body 105. The connection circuits could be utilized to divide the lead 100 into small lengths so that the wire conductors within lead body act as smaller antennas which do not resonate at the MRI frequency.

Figure 8:
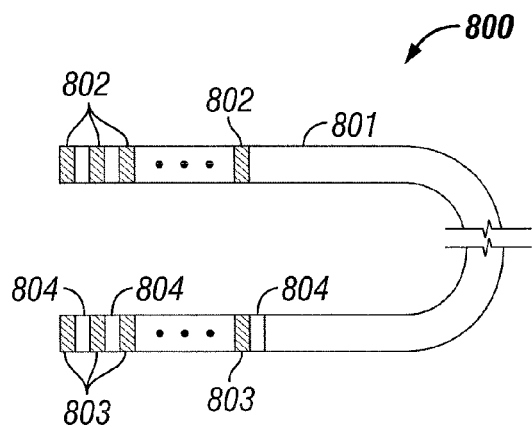
FIG. 8 depicts a percutaneous lead according to one representative embodiment.

Also, although an embodiment has been discussed in regard to a paddle lead, suitable MRI limiting functionality could be implemented within a percutaneous lead, a cortical lead, or a deep brain stimulation (DBS) lead according to some alternative embodiments. For example, FIG. 8 depicts percutaneous lead 800 adapted according to one representative embodiment. Percutaneous lead 800 comprises lead body 801 with a plurality of terminals 802 disposed at the proximal end of percutaneous lead 800. At the distal end of lead 800, a plurality of electrodes 803 are provided. Each electrode 803 is preferably selectively coupled to a conductive wire (not shown) of the lead body through a magnetostrictive switch element 804. When a sufficiently strong magnetic field is detected by the magnetostrictive material, MRI induced current is prevented from being conducted through a given electrode 803 into its corresponding wire conductor of lead body 801.

Figure 4:
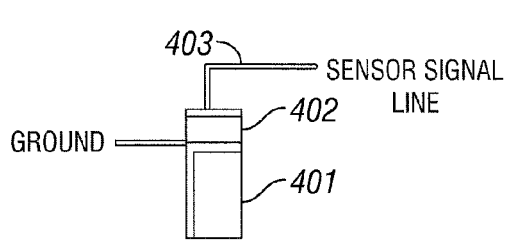
FIG. 4 depicts a circuit containing a piezo element mechanically contacted by magnetostrictive material according to one representative embodiment.

In an alternative embodiment, magnetostrictive material may be utilized to generate a control signal that controls switching operations to limit MRI-induced current. For example, in circuit 400 as shown in FIG. 4, magnetostrictive material 401 may be utilized to effect piezoelectric element 401. The presence of a magnetic field causes deformation of magnetostrictive material 401. The deformation places a strain on piezoelectric element 401 which generates a voltage in response to the strain. The voltage can then be communicated along sensor signal line 403 for detection utilizing suitable circuitry (e.g., an analog-to-digital converter and a microprocessor, or simple voltage-triggered switch).

Figure 7:
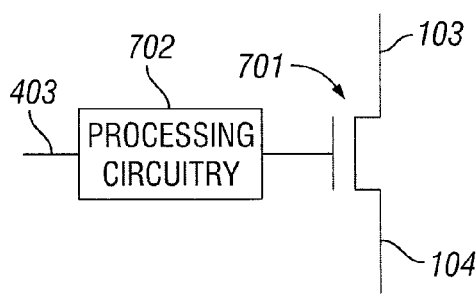
FIG. 7 depicts a current limiting circuit controlled according to one representative embodiment.

Alternatively, the voltage can be provided (possibly in amplified and filtered form) to control a current limiting device. For example, as shown in FIG. 7, the sensor signal is preferably amplified and rectified by processing circuitry 702 and is provided to the gate of field effect transistor (FET) 701. As the magnetic field increases, the output from processing circuitry 702 increases and the channel impedance of FET 701 is increased. Preferably at high magnetic field strengths, the impedance of the channel of FET 701 is sufficiently high that relatively little current flows between the source and drain. In this manner, FET 701 essentially functions as a choke to control the current in response to the detection of a sufficiently strong magnetic field. Although FET 701 is shown between lines 103 and 104 in FIG. 7, such current control could be employed at any suitable location with a stimulation system or device.

Figure 5A:
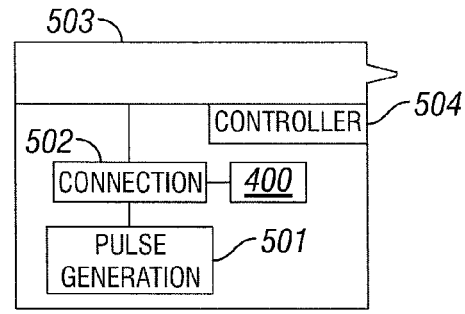
FIGS. 5A-5B depict implantable pulse generators according to some representative embodiments.

FIG. 5A depicts pulse generator 500 that utilizes such a sensor signal according to one representative embodiment. FIG. 5A depicts pulse generation circuitry 501 which generates electrical pulses for stimulation of patient tissue. The electrical pulses are switched through connection circuitry 502 (e.g., a switch matrix) for coupling to one or multiple electrodes through the electrical connections of header structure 503. Connection circuitry 502 is controlled, in part, by circuit 400. Specifically, if magnetic field is detected, connection circuitry 502 is controlled by controller 504 to create an open circuit condition utilizing its switches thereby preventing MRI-induced current from being conducted by the "can" of pulse generator 500.

Figure 5B:
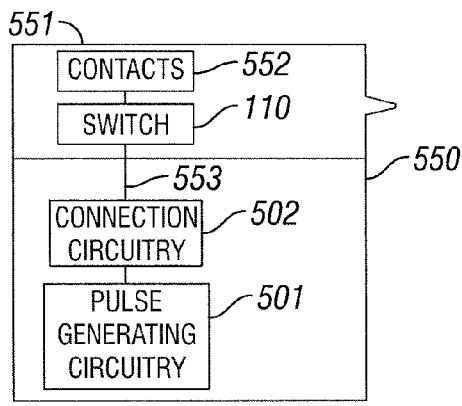

FIG. 5B depicts pulse generator 550 according to an alternative embodiment. Pulse generator 550 comprises header 551 modified to limit MRI-induced current. Specifically, instead of connecting feedthrough wire(s) 553 directly to the electrical contacts 552 that connect to the terminals of a stimulation lead, the feedthrough wire(s) 553 are connected to contacts 552 through switch 110. Accordingly, if a sufficiently strong magnetic field is present, the stimulation lead will no longer be in electrical contact with pulse generating circuitry 501 and, hence, current cannot flow from the lead to the "can" of the pulse generator 550. Thus, eddy current is limited by the operation of switch 110.

Figure 6:
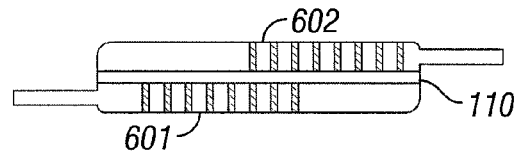
FIG. 6 depicts an extension connector according to one representative embodiment.

In an alternative embodiment, an "extension" connector may be adapted according to one representative embodiment to limit MRI-induced current. As shown in FIG. 6, extension connector 600 is adapted to electrically couple to the electrodes of an "extension" lead using contacts 601. Extension connector 600 preferably comprises an outer housing or body of biocompatible, biostable polymer that houses electrical contacts for a stimulation lead and an extension lead. Extension connector 600 is adapted to electrically couple to the terminals of a lead using contacts 602. Switching structure 110 is disposed between contacts 601 and 602 to control the electrical coupling between contacts 601 and 602 in response to the presence of a magnetic field. The detection of the electrical field may be utilized by the switching structure to disconnect the electrical couplings or shunt the MRI-induced current to an indifferent electrode (not shown) on the body of connector 600 as examples.

The use of magnetostrictive elements to limit or control MRI-induced current may be advantageous for a number of reasons. For example, the magnetostrictive effect is an intrinsic property at the molecular level. When the magnetostrictive material reaches its maximum dimension (i.e., all magnetic poles aligned), then further increases in the magnetic field have no effect. The magnetostrictive effect allows a single switch to work for a variety of commercially available MRI systems. Also, the use of magnetostrictive elements is advantageous because the particular RF frequency of an MRI system does not effect the operation of the switch. Additionally, certain embodiments that utilize magnetostrictive elements do not require electrical power to function. Magnetostrictive elements are robust mechanically. In contrast, conventional "reed switches" have been used to detect magnetic fields to control the operations of pulse generator systems. Reed switches utilize ferromagnetic material. The magnetization of the ferromagnetic material can be permanently changed in the large magnetic field of MRI systems and, thereby, the reed switches can become non-functional. Reed switches tend to be the least reliable components in a pulse generator and are susceptible to "sticking" in a strong magnetic field. Also, reed switches are relatively large thereby complicating the design of implantable medical devices.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A stimulation lead for delivering electrical pulses from a pulse generator to tissue of a patient, comprising:
    a plurality of electrodes;
    a plurality of terminals;
    a plurality of conductors electrically coupling the plurality of electrodes with the plurality of terminals;
    a lead body of insulative material for enclosing the plurality of conductors; and
    at least one magnetic-field actuated switch for limiting MRI-induced current between the plurality of electrodes and the plurality of terminals, wherein the magnetic-field actuated switch is actuated by magnetostrictive material.

2. The stimulation lead of claim 1 wherein the magnetic-field actuated switch mechanically decouples electrical connections between the plurality of electrodes and the plurality of conductors.

3. The stimulation lead of claim 1 wherein the magnetic-field actuated switch controls a current shunt to shunt MRI-induced current to a different electrode where the current can safely flow.

4. The stimulation lead of claim 1 wherein the magnetic-field actuated switch directly or indirectly controls the capacitance of the circuit.

5. The stimulation lead of claim 4 wherein the magnetic-field actuated switch creates the open-circuit condition in the presence of a magnetic field greater than 0.5 Tesla.

6. The stimulation lead of claim 1 wherein the magnetic-field actuated switch directly or indirectly controls the inductance of the circuit, thereby creating a low-pass filter.

7. The stimulation lead of claim 1 wherein the magnetic-field actuated switch creates an open-circuit condition in the presence of a magnetic field of sufficient strength.

8. The stimulation lead of claim 1 wherein the magnetic-field actuated switch is operable to cause the plurality of conductors to possess a shorter antenna length in the presence of a magnetic field of sufficient strength.

9. The stimulation lead of claim 1 wherein the magnetic-field actuated switch is disposed at a distal region of the stimulation lead.

10. The stimulation lead of claim 1 wherein the magnetostrictive material is a terbium, iron, and dysprosium alloy.

11. The stimulation lead of claim 1 wherein the plurality of electrodes are disposed on a paddle structure and the magnetic-field actuated switch is disposed at an end of the paddle structure adjacent to where the plurality of conductors meet the paddle structure.

12. The stimulation lead of claim 1 wherein at least one magnetic-field actuated switch is integrated on a micro-electrical-mechanical (MEMs) device.

13. The stimulation lead of claim 1 wherein the magnetic-field actuated switch contains means permitting the magnetostrictive material to rotate to align with the magnetic field.

* * * * *